United States Patent [19]

Suzuki et al.

[11] Patent Number: 4,954,522

[45] Date of Patent: Sep. 4, 1990

[54] LYOPHILIZED PREPARATION OF PLATINUM COMPOUND

[75] Inventors: Shintaro Suzuki; Noriaki Yanagisawa; Taka'aki Ohkuma, all of Tokyo, Japan

[73] Assignee: Nippon Kayaku Kabushiki Kaisha, Tokyo, Japan

[21] Appl. No.: 275,008

[22] Filed: Nov. 22, 1988

[30] Foreign Application Priority Data

Dec. 3, 1987 [JP] Japan ............................ 62-304509

[51] Int. Cl.$^5$ ............................................ A61K 31/28
[52] U.S. Cl. .................................................... 514/492
[58] Field of Search ......................................... 514/492

[56] References Cited

U.S. PATENT DOCUMENTS

| | | | |
|---|---|---|---|
| 4,310,515 | 1/1982 | Granatek et al. | 424/131 |
| 4,315,002 | 2/1982 | Maurer | 424/181 |
| 4,696,918 | 9/1987 | Stoddart et al. | 514/58 |
| 4,737,589 | 4/1988 | Nowatari et al. | 558/137 |
| 4,737,589 | 4/1988 | Nowatari et al. | 556/137 |
| 4,767,874 | 8/1988 | Shima et al. | 556/137 |

OTHER PUBLICATIONS

Chemical Abstracts 107:161694u, (11/2/87).

*Primary Examiner*—Jerome D. Goldberg
*Attorney, Agent, or Firm*—Henry C. Nields

[57] ABSTRACT

The present invention relates to a lyophilized preparation comprising cis-1,1-cyclobutanedicarboxylate-(2R)-2-methyl-1,4-butanediamine platinum (II), which is useful as an antitumor drug, and dextran. This preparation has a greatly improved resolubility.

3 Claims, No Drawings

LYOPHILIZED PREPARATION OF PLATINUM COMPOUND

BACKGROUND OF THE INVENTION

1. Field of the Invention

The present invention relates to a lyophilized preparation comprising cis-1,1-cyclobutanedicarboxylate-(2R)-2-methyl-1,4-butanediamine platinum (II) (hereinafter referred to as the platinum compound) which is useful as an antitumor drug.

2. Description of the Prior Art

Generally, preparations for injection are prepared in the form of a solution, a lypophilized preparation or a powder preparation.

The platinum compound is relatively unstable in aqueous solutions so that it is highly desirable that the platinum compound be used in the form of a lyophilized preparation or a powdery preparation of its bulk drug powder, because the preparation is usually stored at room temperature over a long period of time. However, a preparation obtained merely by lyophilizing an aqueous solution of the platinum compound dissolves in water so slowly that it is necessary to conduct heating or stirring over a long period of time, when the preparation is to be redissolved. Furthermore the powder preparation dissolves more slowly than the lyophilized preparation so that redissolution is further difficult.

SUMMARY OF THE INVENTION

The inventors made intensive studies to find out that when dextran is added to a solution of the platinum compound and the solution is lyophilized, the resulting preparation has a greatly improved resolubility.

The present invention has been accomplished on the basis of the above-described finding. Namely, the present invention relates to a lyophilized preparation comprising dextran and cis-1,1-cyclobutanedicarboxylate-(2R)-2-methyl-1,4-butanediamine platinum (II).

DETAILED DESCRIPTION OF THE INVENTION

Dextran which can be used in the present invention has a molecular weight of, e.g., 40,000 to 150,000, preferably 40,000 to 70,000.

The amount of dextran to be added is not less than about 0.2 part by weight, preferably not less than about 0.5 part by weight per part by weight of the platinum compound in order to obtain a sufficient effect in the invention. Although the addition of an excess amount of the additive does not have any adverse effect, it will cause lowering in the efficiency of lyophilization and a container having a large volume must be used for preparation. Accordingly, the practical upper limit is about 5 parts by weight, preferably about 2 parts by weight per part by weight of the platinum compound.

The preparation of the present invention can be produced in the following manner. The platinum compound and dextran are mixed with optionally, conventional excipients, extenders, tonicity agents, etc. The mixture is dissolved in distilled water for injection at a temperature of 15° to 70° C. to obtain the solution containing 0.1–1.4%, preferably 0.5–1.4% of the platinum compound and the resulting solution is made germfree or sterilized. The treated solution is then freezed at a temperature not higher than 0° C., preferably from −10° to −40° C. and dried in vacuo at a shelf temperature of −40° to 40° C. by a conventional method.

Now, the effect of the invention will be illustrated by referring to Experimental Example.

EXPERIMENTAL EXAMPLE 10 ml of distilled water for injection was added to each preparation of Examples 1 to 4 and Referential Examples 1 and 2 which will be described hereinafter. The mixture was shaken and a time taken until the solid was dissolved and disappeared was measured. The results are shown in the following Table.

| Preparation | Time taken for dissolution |
|---|---|
| Example 1 | 10 sec |
| Example 2 | 10 sec |
| Example 3 | 15 sec |
| Example 4 | 15 sec |
| Ref. Example 1 | 5 min |
| Ref. Example 2 | 30 min or longer |

It is apparent from the Table that all of the solids in the preparations (Examples 1 to 4) of the present invention are rapidly dissolved within 15 sec, while the preparation of Referential Example 1 takes 5 min. to dissolve in water and some part of the preparation of Referential Example 2 is left undissolved even after 30 min. Accordingly, the present invention can provide a lyophilized preparation of the platinum compound, which has an improved solubility.

EXAMPLE 1

10 g of the platinum compound and 10 g of Dextran 40 were dissolved in distilled water for injection to a volume of one liter in total. The resulting solution was filtered through a membrane filter to remove germs. 10 ml of the solution was put into each of 20-ml glass vials and lyophilized by a conventional method to obtain a preparation.

EXAMPLE 2

10 g of the platinum compound and 20 g of Dextran 40 were dissolved in distilled water for injection to a volume of one liter in total. The resulting solution was filtered through a membrane filter to remove germs. 10 ml of the solution was put into each of 20-ml glass vials and lyophilized by a conventional method to obtain a preparation.

EXAMPLE 3

10 g of the platinum compound and 5 g of Dextran 70 were dissolved in distilled water for injection to a volume of one liter in total. The resulting solution was filtered through a membrane filter to remove germs. 10 ml of the solution was put into each of 20-ml glass vials and lyophilized by a conventional method to obtain a preparation.

EXAMPLE 4

10 g of the platinum compound and 20 g of Dextran 70 were dissolved in distilled water for injection to a volume of one liter in total. The resulting solution was filtered through a membrane filter to remove germs. 10 ml of the solution was put into each of 20-ml glass vials and lyophilized by a conventional method to obtain a preparation.

REFERENTIAL EXAMPLE 1

10 g of the platinum compound was dissolved in distilled water for injection to a volume of one liter in total. The resulting solution was filtered through a membrane filter to remove germs. 10 ml of the solution was put into each of 20-ml glass vials and lyophilized by a conventional method to obtain a preparation.

REFERENTIAL EXAMPLE 2

100 mg of the bulk drug powder of the platinum compound sterilely produced was put into each of 20-ml glass vials to obtain a preparation.

What is claimed is:

1. A lyophilized preparation comprising dextrane having a molecular weight of 40,000 to 150,000 and cis-1,1-cyclobutanedicarboxylate(2R)-2-methyl-1,4-butanediamine platinum (II), and the amount of dextrane being from about 0.2 part to about 5 parts per part by weight of the platinum compound, wherein said preparation is easily redissolved in a period of time within a range substantially less than 5 minutes and extending down to a period of time as short as 10–15 seconds.

2. A preparation according to claim 1, wherein the amount of dextrane to be added is about 0.5 part by weight to about 5 parts by weight per 1 part by weight of the platinum compound.

3. A preparation according to claim 1, wherein the amount of the dextrane to be added is about 0.5 part by weight to about 2 parts by weight per 1 part by weight of the platinum compound.

* * * * *